(12) United States Patent
Bencini et al.

(10) Patent No.: US 7,972,323 B1
(45) Date of Patent: *Jul. 5, 2011

(54) STEERABLE DEVICE FOR INTRODUCING DIAGNOSTIC AND THERAPEUTIC APPARATUS INTO THE BODY

(75) Inventors: Robert F. Bencini, Sunnyvale, CA (US); Russell B. Thompson, Los Altos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/548,465

(22) Filed: Apr. 13, 2000

Related U.S. Application Data

(63) Continuation-in-part of application No. 09/165,652, filed on Oct. 2, 1998, now Pat. No. 6,544,215.

(51) Int. Cl.
*A61M 25/00* (2006.01)
(52) U.S. Cl. ............ 604/524; 604/95.01; 604/95.04; 604/523
(58) Field of Classification Search .......... 604/95.01, 604/95.02, 100.01, 164.01, 528, 95.04, 264, 604/523, 164.13, 165.02, 525, 95.03, 524, 604/526, 527, 529, 530, 531, 532
See application file for complete search history.

(56) References Cited

U.S. PATENT DOCUMENTS

| | | | |
|---|---|---|---|
| 3,470,876 A | 10/1969 | Barchilon | |
| 4,586,923 A | 5/1986 | Gould et al. | |
| 4,664,113 A | 5/1987 | Frisbie et al. | |
| 4,719,924 A | 1/1988 | Crittenden et al. | |
| 4,723,936 A | 2/1988 | Buchbinder et al. | |
| 4,757,827 A | 7/1988 | Buchbinder et al. | |
| 4,898,577 A | 2/1990 | Badger | |
| 4,906,230 A | 3/1990 | Maloney et al. | |
| 4,920,980 A | 5/1990 | Jackowski | |
| 4,934,340 A * | 6/1990 | Ebling et al. | 600/151 |
| 4,960,411 A | 10/1990 | Buchbinder | |
| 5,030,204 A | 7/1991 | Badger et al. | |
| 5,114,403 A | 5/1992 | Clarke et al. | |
| 5,114,414 A | 5/1992 | Buchbinder | |
| 5,125,896 A | 6/1992 | Hojeibane | |
| 5,199,950 A | 4/1993 | Schmitt et al. | |
| 5,231,989 A | 8/1993 | Middleman et al. | |
| 5,255,668 A * | 10/1993 | Umeda | 600/139 |
| 5,318,525 A | 6/1994 | West | |
| 5,336,182 A * | 8/1994 | Lundquist et al. | 604/528 |
| 5,342,299 A | 8/1994 | Snoke et al. | |

(Continued)

FOREIGN PATENT DOCUMENTS

DE  43 36 040 A1  4/1995

(Continued)

OTHER PUBLICATIONS

PCT Invitation to Pay Additional Fees including Search Report dated Apr. 3, 2002 for PCT application Ser. No. PCT/EP01/04247.
PCT International Search Report dated May 30, 2002 for PCT application Ser. No. PCT/EP01/04247.

(Continued)

*Primary Examiner* — Kevin C Sirmons
*Assistant Examiner* — Laura C Schell
(74) *Attorney, Agent, or Firm* — Henricks, Slavin & Holmes LLP

(57) ABSTRACT

An apparatus including an elongate body having a lumen extending therethrough and a steering wire associated with the distal portion of the elongate body.

41 Claims, 15 Drawing Sheets

U.S. PATENT DOCUMENTS

| | | | |
|---|---|---|---|
| 5,345,945 A | | 9/1994 | Hodgson et al. |
| 5,363,861 A | | 11/1994 | Edwards |
| 5,368,564 A | | 11/1994 | Savage |
| 5,378,234 A | * | 1/1995 | Hammerslag et al. ..... 604/95.04 |
| 5,381,782 A | | 1/1995 | DeLaRama et al. |
| 5,391,146 A | | 2/1995 | That et al. |
| 5,395,327 A | | 3/1995 | Lundquist |
| 5,409,483 A | | 4/1995 | Campbell et al. |
| 5,419,340 A | * | 5/1995 | Stevens ................ 600/585 |
| 5,419,764 A | | 5/1995 | Roll |
| 5,431,168 A | * | 7/1995 | Webster, Jr. .............. 600/435 |
| 5,472,017 A | * | 12/1995 | Kovalcheck ............. 138/103 |
| 5,477,856 A | | 12/1995 | Lundquist |
| 5,484,407 A | | 1/1996 | Osypka |
| 5,507,725 A | * | 4/1996 | Savage et al. ........... 604/95.04 |
| 5,531,686 A | | 7/1996 | Lundquist et al. |
| 5,531,687 A | | 7/1996 | Snoke et al. |
| 5,603,697 A | | 2/1997 | Grundy |
| 5,611,777 A | | 3/1997 | Bowden |
| 5,636,634 A | | 6/1997 | Kordis |
| 5,676,653 A | | 10/1997 | Taylor et al. |
| 5,690,642 A | * | 11/1997 | Osborne et al. ......... 604/103.04 |
| 5,695,483 A | * | 12/1997 | Samson ................. 604/526 |
| 5,702,433 A | | 12/1997 | Taylor et al. |
| 5,820,591 A | | 10/1998 | Thompson et al. |
| 5,827,278 A | | 10/1998 | Webster |
| 5,843,020 A | | 12/1998 | Tu et al. |
| 5,848,986 A | * | 12/1998 | Lundquist et al. ............. 604/22 |
| 5,855,560 A | | 1/1999 | Idaomi et al. |
| 5,857,997 A | | 1/1999 | Cimino |
| 5,876,340 A | | 3/1999 | Tu et al. |
| 5,876,373 A | | 3/1999 | Giba et al. |
| 5,882,333 A | | 3/1999 | Schaer et al. |
| 5,897,529 A | | 4/1999 | Ponzi |
| 5,908,405 A | | 6/1999 | Imran et al. |
| 5,916,147 A | | 6/1999 | Boury |
| 5,935,102 A | | 8/1999 | Bowden et al. |
| 5,938,616 A | | 8/1999 | Eaton et al. |
| 6,030,360 A | | 2/2000 | Biggs |
| 6,059,739 A | | 5/2000 | Baumann |
| 6,066,125 A | | 5/2000 | Webster, Jr. |
| 6,083,170 A | | 7/2000 | Ben-Haim |
| 6,146,355 A | | 11/2000 | Biggs |
| 6,213,974 B1 | | 4/2001 | Smith et al. |
| 6,450,948 B1 | * | 9/2002 | Matsuura et al. ............. 600/139 |
| 6,491,681 B1 | | 12/2002 | Kunis et al. |
| 6,540,778 B1 | * | 4/2003 | Quiachon et al. ........... 623/1.23 |
| 6,544,215 B1 | | 4/2003 | Bencini et al. |
| 6,554,794 B1 | * | 4/2003 | Mueller et al. ............ 604/95.04 |
| 6,991,616 B2 | | 1/2006 | Bencini et al. |
| 7,695,451 B2 | | 4/2010 | Bencini et al. |
| 7,731,682 B2 | | 6/2010 | Bencini et al. |
| 2006/0184107 A1 | | 8/2006 | Bencini et al. |
| 2008/0188800 A1 | | 8/2008 | Bencini et al. |
| 2008/0188801 A1 | | 8/2008 | Bencini et al. |

FOREIGN PATENT DOCUMENTS

| | | |
|---|---|---|
| EP | 0 489 937 B1 | 6/1995 |
| EP | 0689851 A | 1/1996 |
| EP | 0815895 A | 1/1998 |
| WO | WO-97/27895 A | 8/1997 |
| WO | WO-99/33509 A | 7/1999 |
| WO | WO-99/62585 | 12/1999 |
| WO | WO 00/06242 | 2/2000 |
| WO | WO 00/15286 | 3/2000 |
| WO | WO 00/18323 | 4/2000 |
| WO | WO-00/22981 | 4/2000 |

OTHER PUBLICATIONS

English language translation of the text of DE 43 36 040 A1.
Office Action dated May 10, 2007 in U.S. Appl. No. 11/304,078.
Office Action dated Nov. 30, 2007 in U.S. Appl. No. 11/304,078.
Office Action dated Feb. 27, 2008 in U.S. Appl. No. 11/304,078.
Office Action dated Jul. 11, 2008 in U.S. Appl. No. 11/304,078.
Office Action dated Nov. 3, 2008 in U.S. Appl. No. 11/304,078.
Office Action dated Jul. 15, 2009 in U.S. Appl. No. 11/304,078.
Office Action dated Jun. 22, 2009 in U.S. Appl. No. 11/923,536.
Office Action dated Mar. 5, 2010 in U.S. Appl. No. 11/923,606.
Office Action dated Aug. 16, 2010 in U.S. Appl. No. 11/923,606.

* cited by examiner

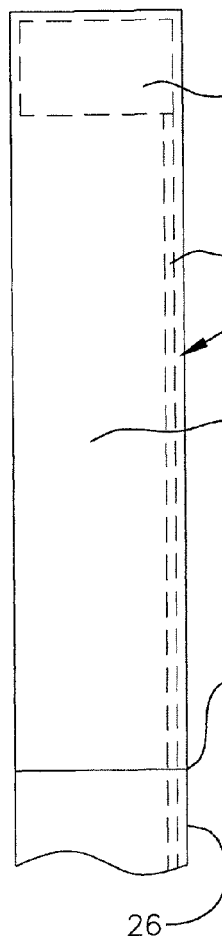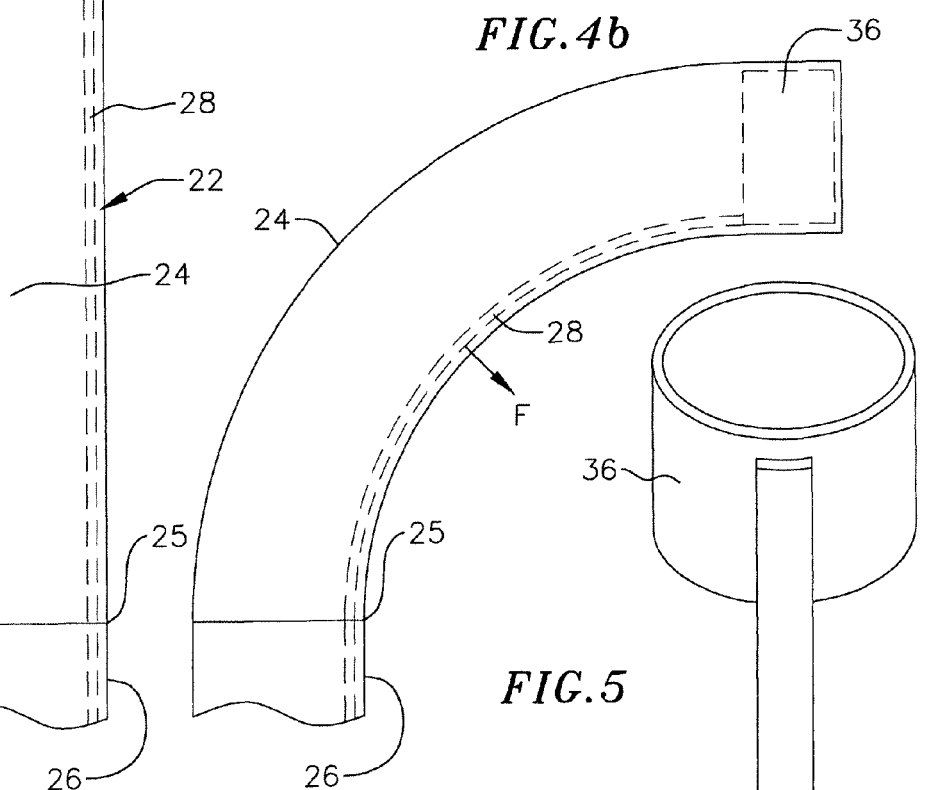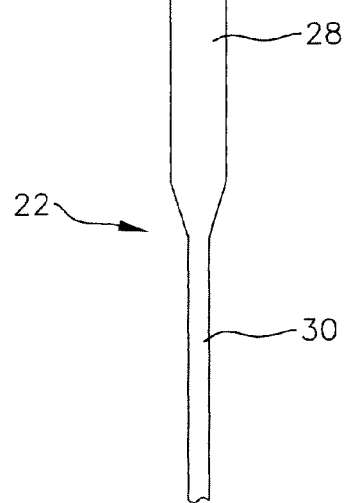

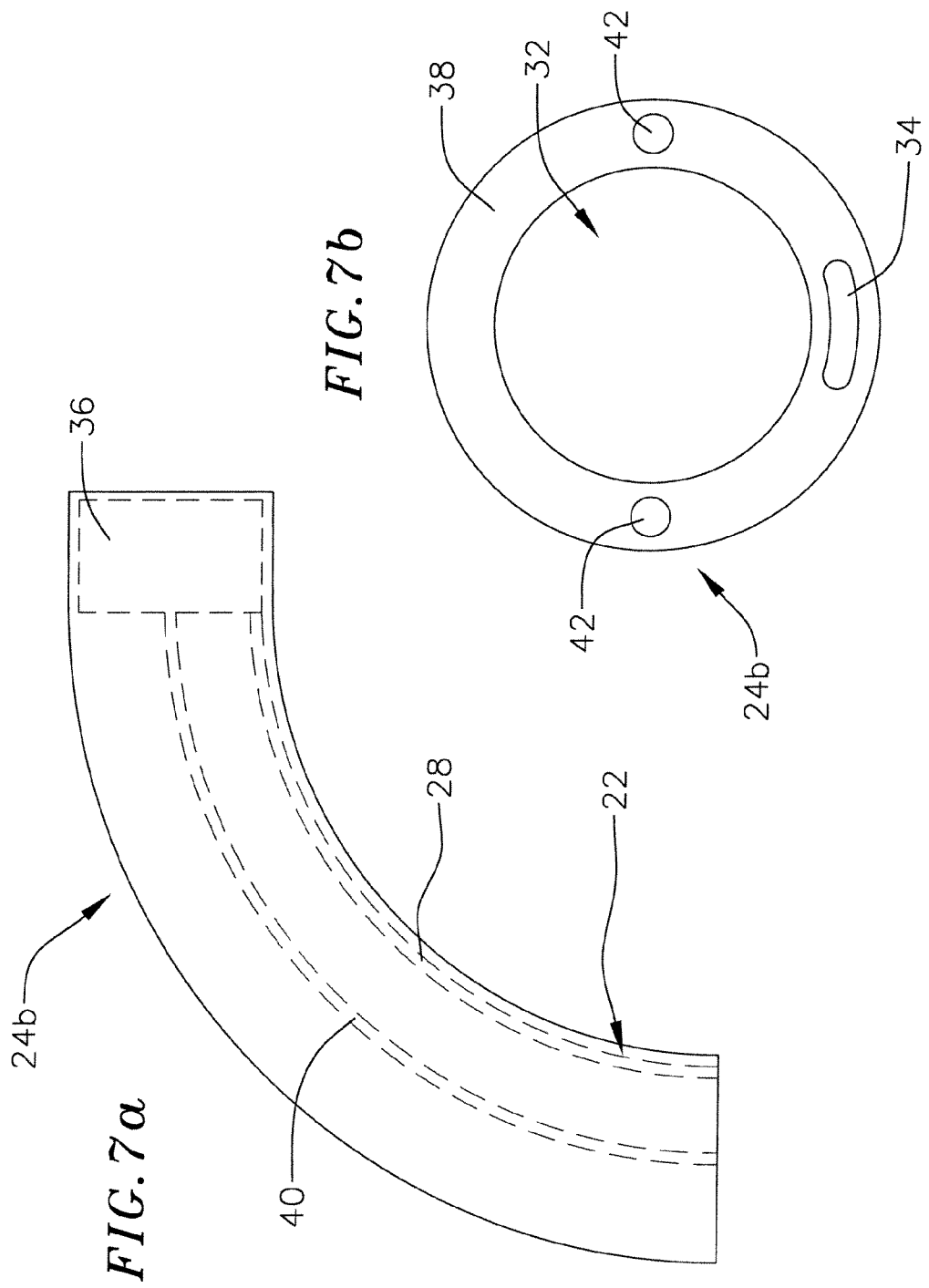

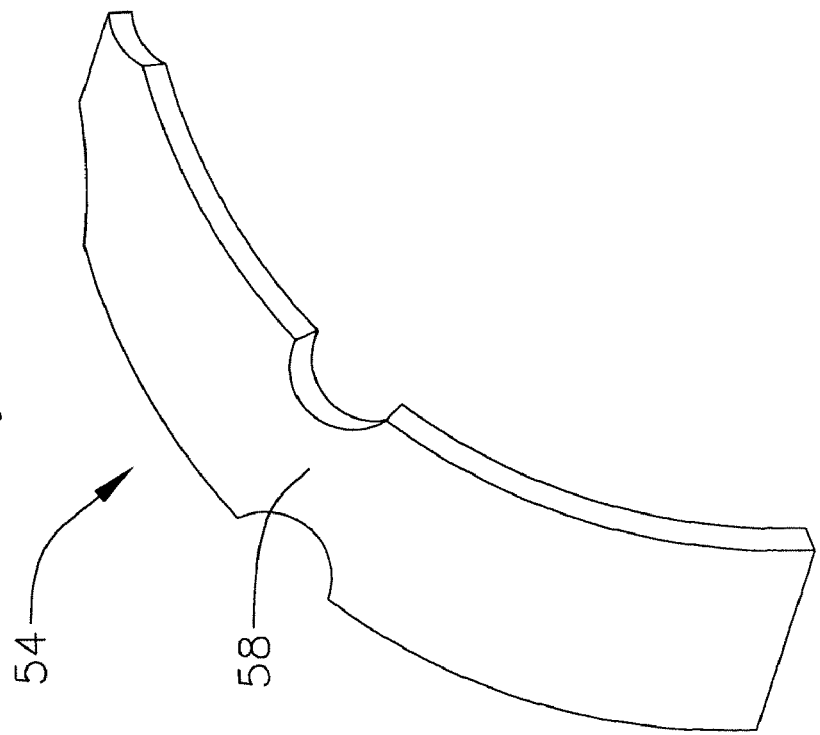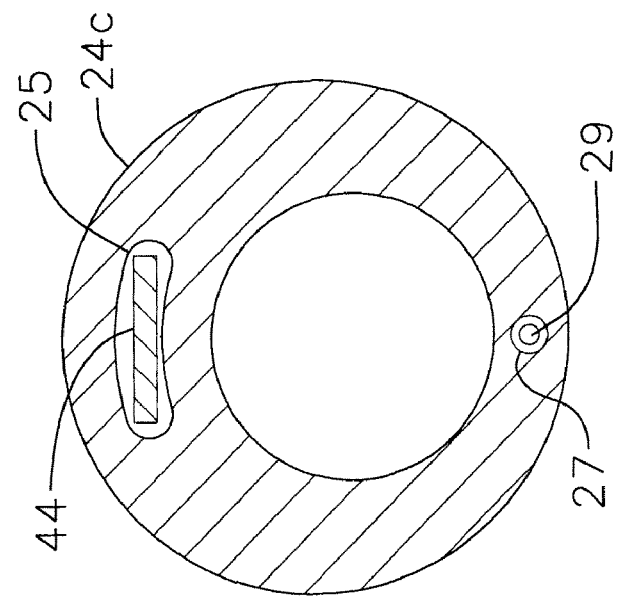

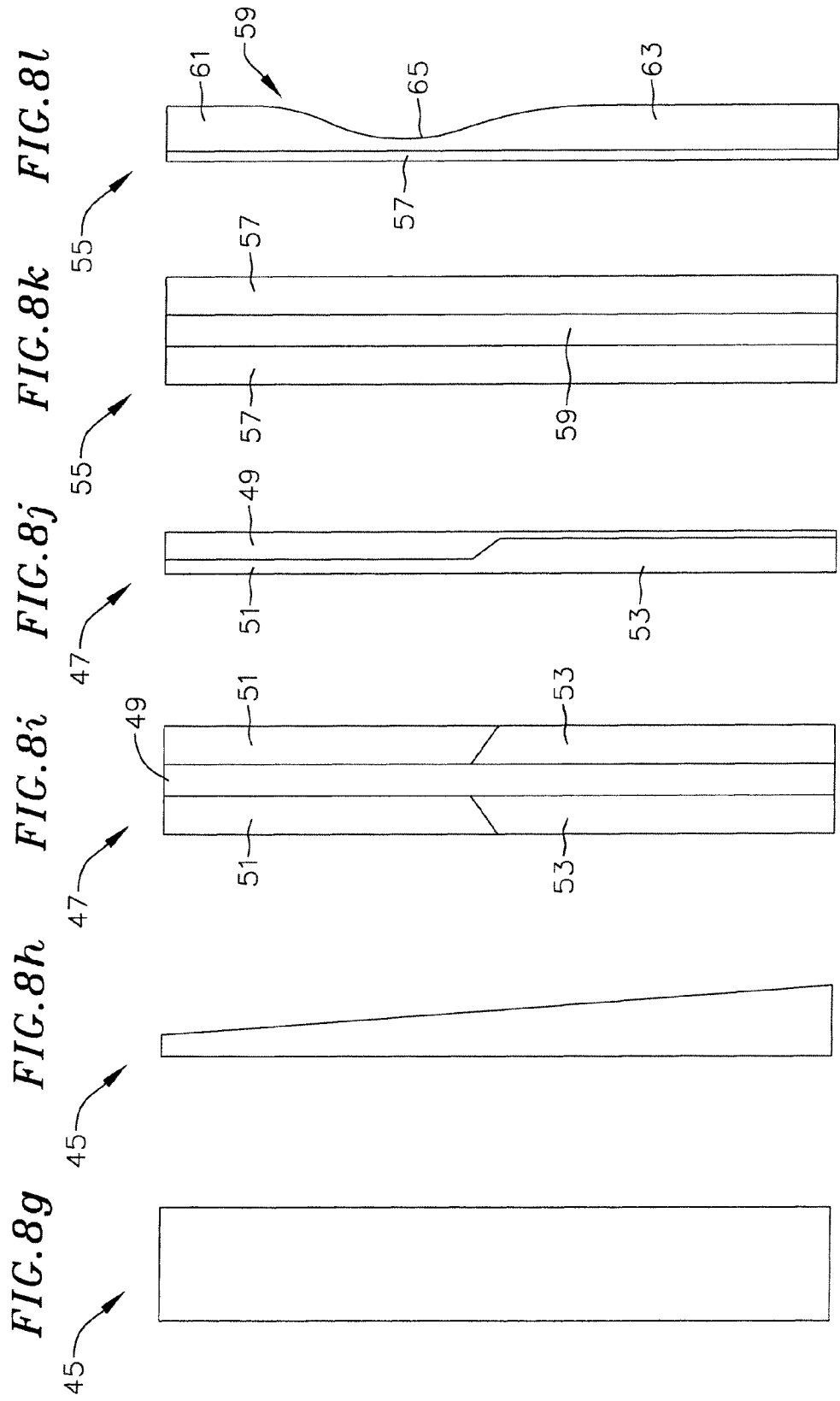

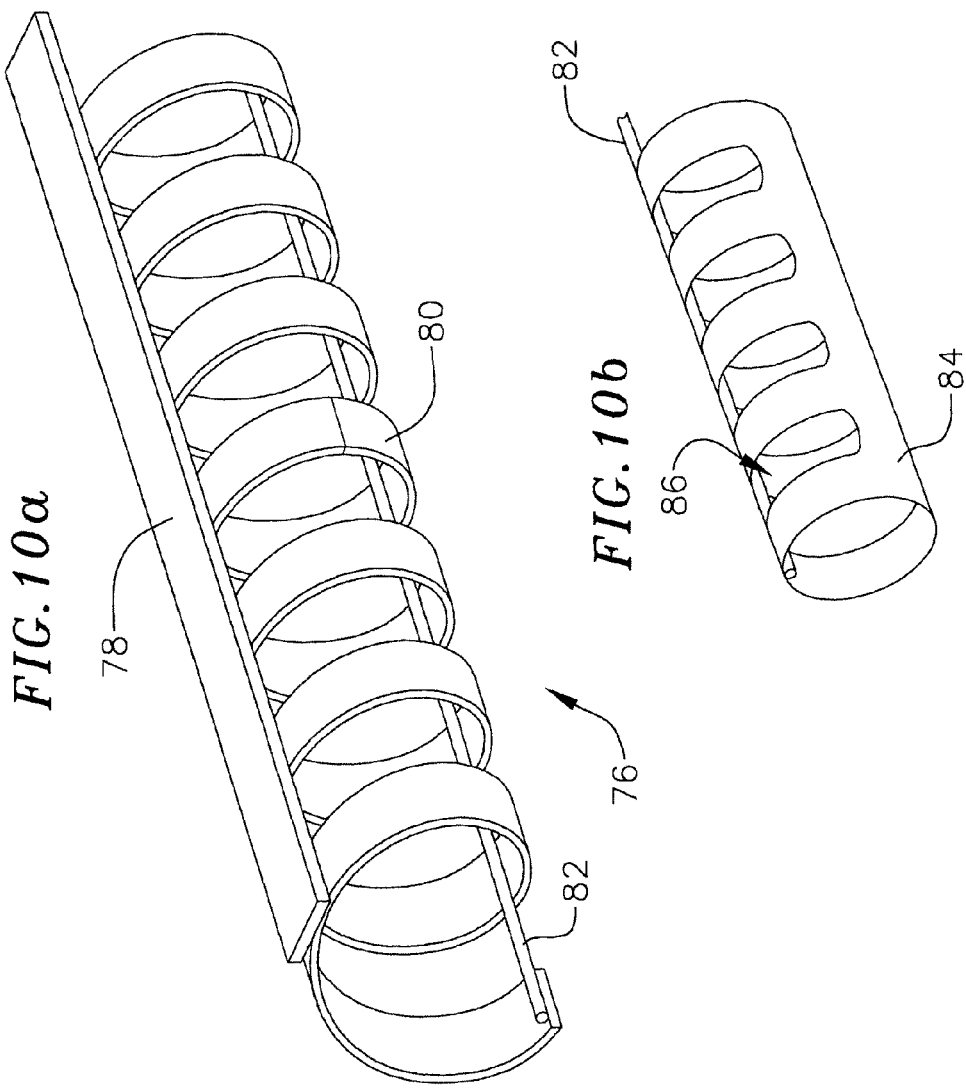

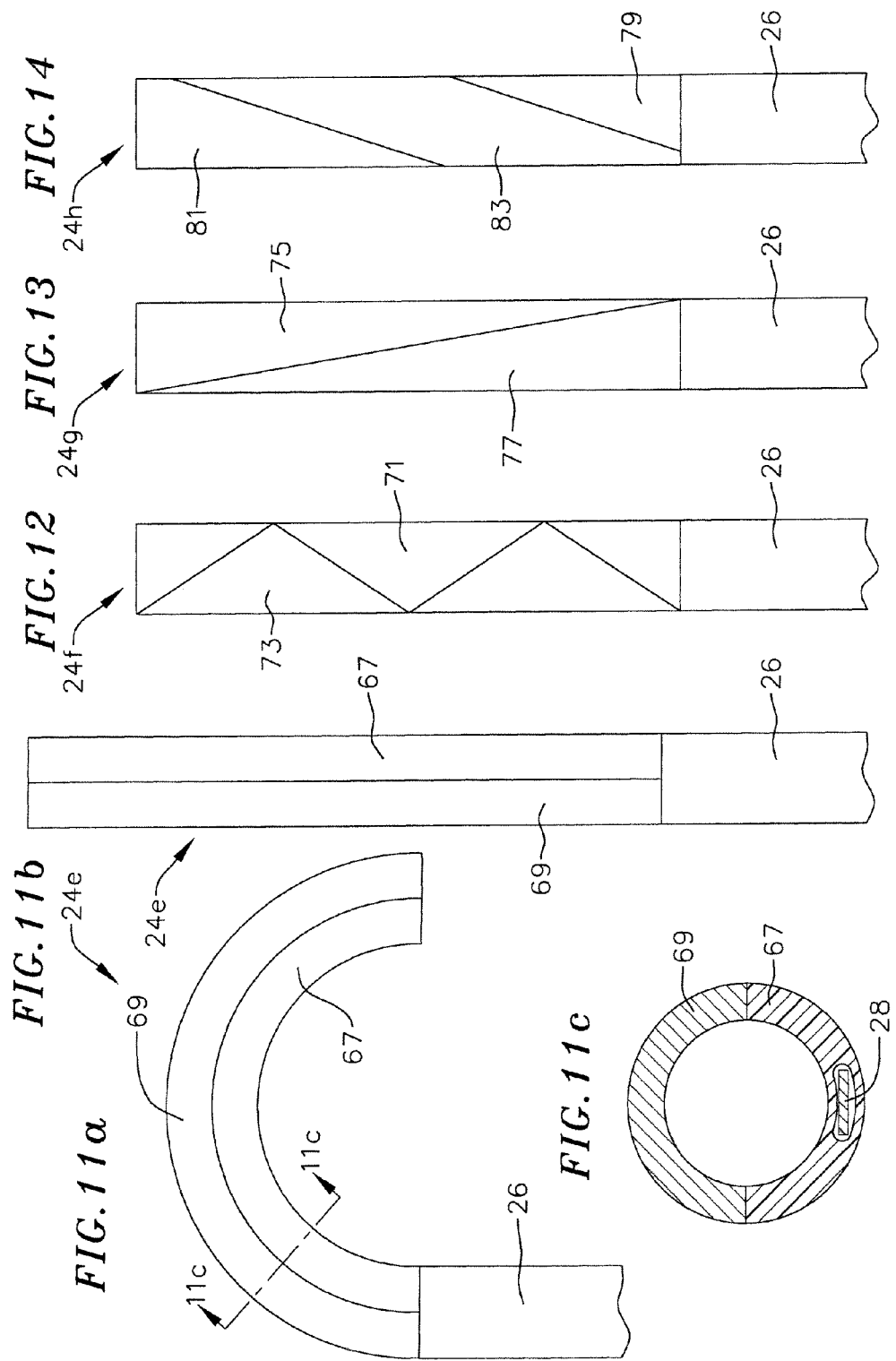

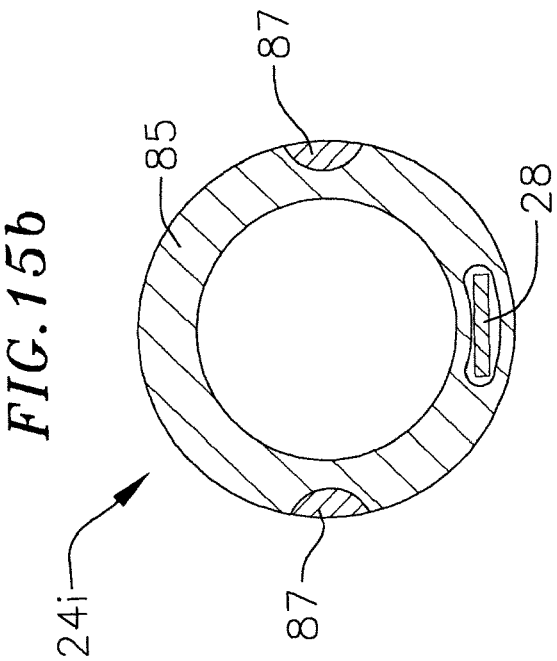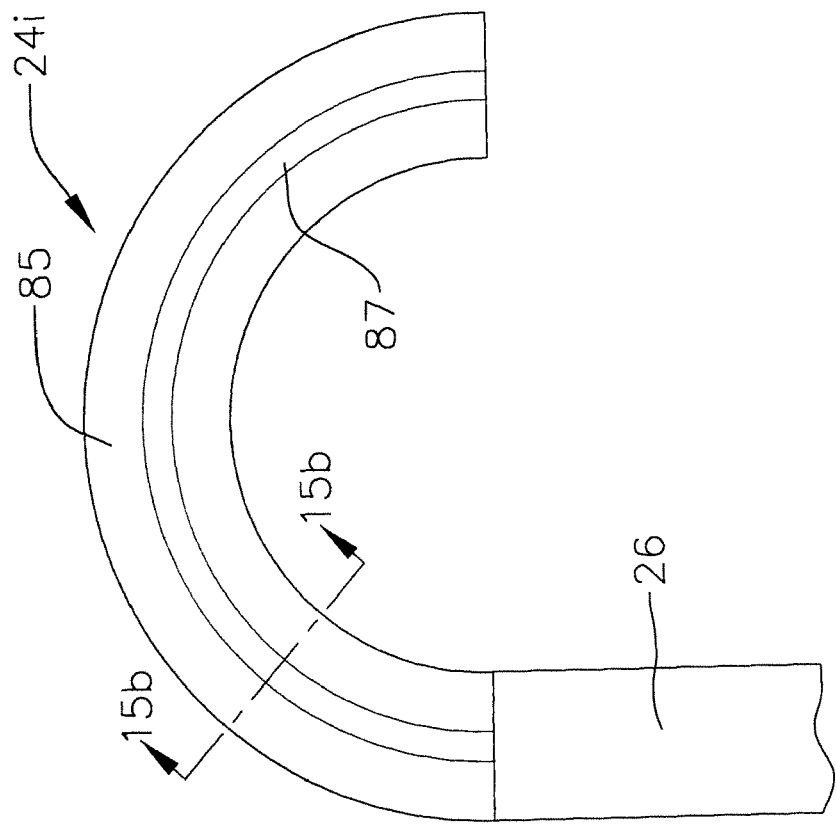

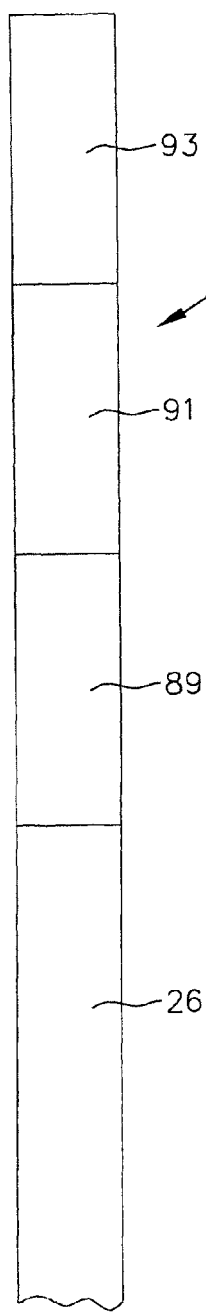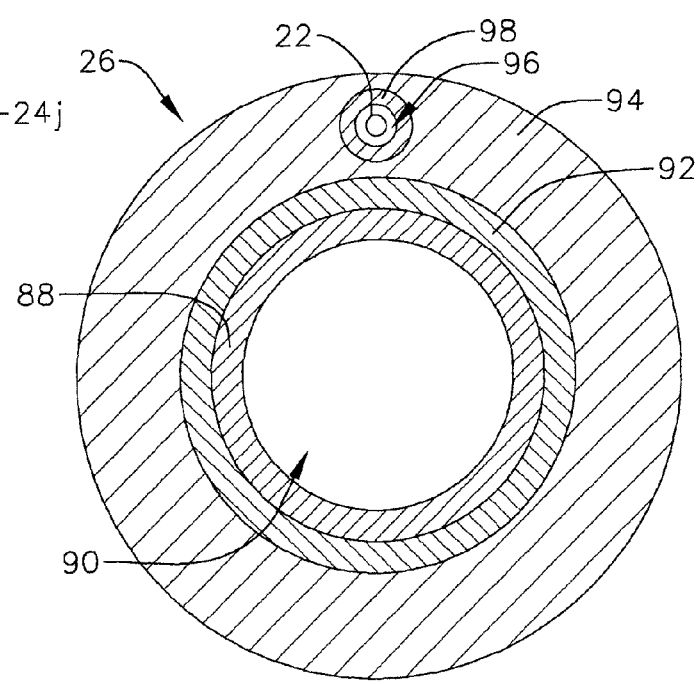

STEERABLE DEVICE FOR INTRODUCING DIAGNOSTIC AND THERAPEUTIC APPARATUS INTO THE BODY

CROSS-REFERENCE TO RELATED APPLICATIONS

This application is a continuation-in-part of U.S. application Ser. No. 09/165,652, filed Oct. 2, 1998, now U.S. Pat. No. 6,544,215, which is incorporated herein by reference.

BACKGROUND OF THE INVENTIONS

1. Field of Inventions

The present inventions relate generally to devices that are used to introduce diagnostic and therapeutic apparatus into the body.

2. Description of the Related Art

There are many instances where physicians must introduce diagnostic and therapeutic apparatus, such as diagnostic and therapeutic electrodes, ultrasound transducers, biopsy devices and other surgical tools, into the body. The diagnostic and therapeutic apparatus are often carried by catheters, which allow physicians to gain access to the body in a minimally invasive manner by way of bodily lumens. In cardiac treatment, for example, a catheter is advanced through a main vein or artery into the region of the heart that is to be treated.

One method of introducing diagnostic and therapeutic apparatus into the body is to introduce a tubular member (typically a "sheath") into the vicinity of the targeted region. A diagnostic or therapeutic apparatus is then passed through the tubular member to the targeted region. If necessary, the diagnostic or therapeutic apparatus may be removed after its function is performed, but the tubular member left in place, so that other apparatus may be advanced to the targeted region to complete the diagnostic and/or therapeutic procedure.

Precise placement of the diagnostic or therapeutic apparatus is very important, especially in those procedures concerning the heart. To that end, some conventional sheaths are guided to the targeted region with a steerable catheter that is located within the sheath lumen. Once the sheath reaches the targeted region, the steerable catheter is removed from the sheath and a catheter carrying the diagnostic or therapeutic apparatus is advanced through the lumen. This type of sheath lacks any onboard steering mechanism. As a result, redeployment of the distal portion of sheath, even to a region in close proximity to the initially targeted region, requires the withdrawal of the diagnostic or therapeutic apparatus and the reintroduction of the steering catheter.

Other conventional sheaths include a steering mechanism that allows the physician to deflect the distal portion of the sheath. The steering mechanism consists primarily of one or more steering wires. One end of each steering wire is secured to the distal end of the sheath, while the other end is secured to a steering control device, such as the rotating cam and steering control knob arrangement commonly found in steerable catheters. Rotation of the control knob causes one of the wires to impart a pulling force on the distal portion of the sheath, thereby causing the distal portion to deflect. To promote steerability, the distal portion of the sheath (which is relatively short) is typically formed from relatively soft, flexible material. Conversely, the proximal portion (which is relatively long) is formed from relatively hard, less flexible material that provides better torque transmission properties.

The inventors herein have determined that there are a number of shortcomings associated with conventional steerable apparatus, such as steerable sheaths, that are used to introduce diagnostic and therapeutic apparatus into the body. For example, it is desirable to provide a sheath or other tubular member having a small outer diameter (OD) in order to limit the size of the entry hole that must be made in the patient's vein or artery and to compensate for the effects of arteriosclerosis. Because the diameter of the lumen, or inner diameter (ID), tends to be a function of the size of the diagnostic and therapeutic apparatus to be introduced into the body, the primary method of reducing the OD is reducing the wall thickness of the tubular member.

Heretofore, efforts to reduce wall thickness have been hampered by the fact that the wall strength of the tubular member distal portion must be sufficient to prevent the steering wire from tearing through the distal portion during deflection. Proposed solutions to the strength problem included the use of harder materials and/or the addition of mechanical devices, such as coils, to the distal portion of the tubular member. The inventors herein have determined that such solutions are less than optimal because they limit the flexibility and, therefore, the steerability of the distal portion of the sheath or other tubular member.

The inventors herein have also determined that the distal portion of the tubular member in conventional steerable apparatus will sometimes buckle during steering operations and do not always return to the neutral position after the steering operation is complete. Moreover, it can be difficult to produce a distal portion that will bend to a specific radius of curvature using conventional structures and manufacturing techniques.

SUMMARY OF THE INVENTIONS

Accordingly, the general object of the present inventions is to provide apparatus that avoids, for practical purposes, the aforementioned problems. In particular, one object of the present inventions is to provide a steerable apparatus for introducing diagnostic and therapeutic apparatus into the body, such as a steerable sheath, having a thinner wall than conventional apparatus without sacrificing steerability.

In order to accomplish some of these and other objectives, an apparatus in accordance with one embodiment of a present invention includes an elongate body having a lumen extending therethrough and a steering wire, having a distal portion defining a non-circular cross-section, associated with the distal portion of the elongate body. In one preferred implementation, the elongate body is a sheath and the distal portion of the steering wire is substantially flat.

The present apparatus provides a number of advantages over conventional steerable apparatus for introducing diagnostic and therapeutic apparatus into the body. For example, the non-circular steering wire distal portion distributes the forces generated during deflection over a greater surface area than a steering wire having a circular cross-section. The redistribution of forces over a greater area reduces the amount strength required to prevent the steering wire from tearing through the distal portion of the tubular members, sheaths or other elongate bodies during deflection. As a result, the present elongate body may be made thinner than the tubular members, sheaths or other elongate bodies in conventional steerable apparatus formed from the same material.

Use of the present non-circular steering wire also prevents out of plane bending. The non-circular portion of the steering wire also provides a larger surface area for attaching the steering wire to the distal portion of the elongate body or an element within the elongate body, thereby making manufacturing easier and, due to the larger bonding area, decreasing the likelihood that the steering wire and elongate body will become disconnected.

In order to accomplish some of these and other objectives, an apparatus in accordance with one embodiment of a present invention includes an elongate body having a lumen extending therethrough, a steering wire associated with the distal portion of the elongate body, and a stiffening member associated with the distal portion of the elongate body. The present apparatus provides a number of advantages over conventional steerable apparatus for introducing diagnostic and therapeutic apparatus into the body. For example, the stiffening member will prevent buckling of the elongate body distal portion during bending. The stiffening member may also be configured such that it will return the elongate body distal portion to a neutral position after a steering operation, influence the curvature of the elongate body during steering, provide a pre-bend in a direction other than the direction in which the distal portion is bent during steering, and increase the torque transmission properties of the distal portion.

In order to accomplish some of these and other objectives, an apparatus in accordance with one embodiment of a present invention includes an elongate body proximal portion, an elongate body distal portion, and a steering wire having a distal portion operably connected to the elongate body distal portion. The elongate body distal portion is formed from distal members with different stiffnesses. Such apparatus provides a number of advantages over conventional steerable apparatus for introducing diagnostic and therapeutic apparatus into the body. For example, the stiffer distal member will prevent buckling of the elongate body distal portion during bending.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIGS. 4a and 4b are side views of the elongate body distal portion illustrated in FIG. 3.

FIG. 5 is a perspective view of a steering wire and steering wire anchoring member assembly in accordance with a preferred embodiment of a present invention.

FIG. 6b is a top view of the elongate body distal portion illustrated in FIG. 6a.

FIG. 7a is a side view of an elongate body distal portion in accordance with still another preferred embodiment of a present invention.

FIG. 7b is a top view of the elongate body distal portion illustrated in FIG. 7a.

FIG. 8e is a section view of an elongate distal body including the stiffening member illustrated in FIG. 8a.

FIG. 8f is a perspective view of the stiffening member illustrated in FIG. 8c with a prebend.

FIGS. 8g and 8h are front elevation and side views of a stiffening member in accordance with a preferred embodiment of a present invention.

FIGS. 8i and 8j are front elevation and side views of a stiffening member in accordance with a preferred embodiment of a present invention.

FIGS. 8k and 8l are front elevation and side views of a stiffening member in accordance with a preferred embodiment of a present invention.

FIG. 10a is a perspective view of another stiffening member in accordance with a preferred embodiment of a present invention.

FIG. 10b is a perspective view of still another stiffening member in accordance with a preferred embodiment of a present invention.

FIG. 11a is a side view of an elongate body distal portion in accordance with a preferred embodiment of a present invention in a bent orientation.

FIG. 11b is a side view of the elongate body distal portion illustrated in FIG. 11a in a straight orientation.

FIG. 11c is a section view take along line 11c-11c in FIG. 11a.

FIGS. 12, 13 and 14 are side views of elongate body distal portions in accordance with preferred embodiments of a present invention.

FIG. 15a is a side view of an elongate body distal portion in accordance with a preferred embodiment of a present invention.

FIG. 15b is a section view take along line 15b-15b in FIG. 15a.

FIG. 16 is a side view of an elongate body distal portion in accordance with a preferred embodiment of a present invention.

FIG. 17 is a section view taken along line 17-17 in FIG. 1.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Overview
II. Elongate Body Distal Portion
III. Elongate Body Proximal Portion
IV. Handle The section titles and overall organization of the present detailed description are for the purpose of convenience only and are not intended to limit the present inventions.

I. Overview

The present inventions may be used within body lumens, chambers or cavities for diagnostic or therapeutic purposes in those instance where access to interior bodily regions is obtained through, for example, the vascular system or alimentary canal and without complex invasive surgical procedures. For example, the inventions herein have application in the diagnosis and treatment of conditions within the heart. The inventions herein also have application in the diagnosis or treatment of ailments of the gastrointestinal tract, prostrate, brain, gall bladder, uterus, and other regions of the body.

Figure 1:
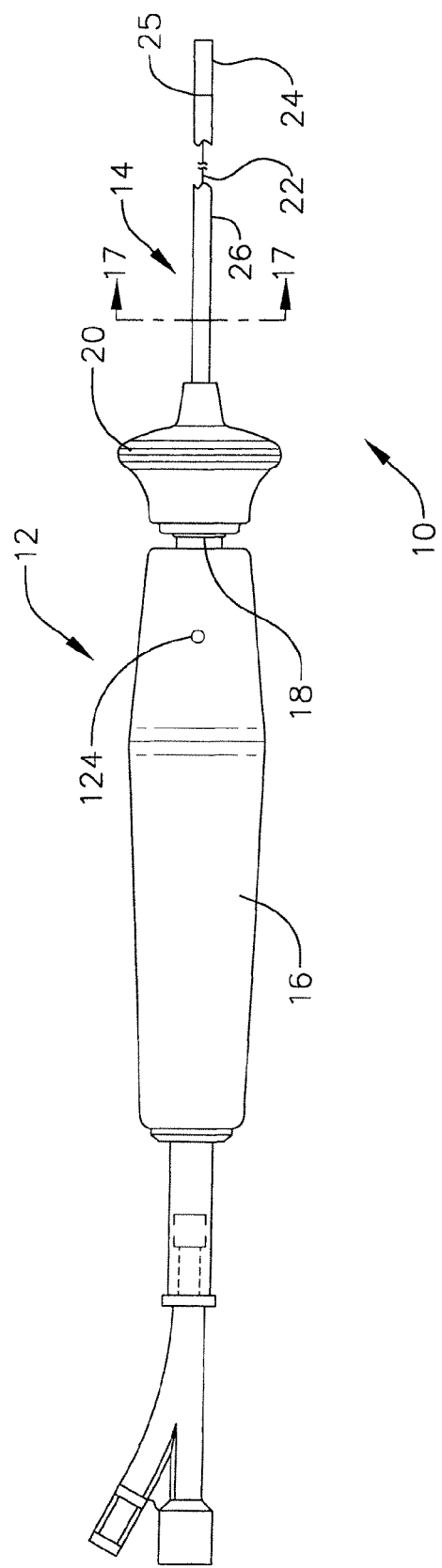
FIG. 1 is a plan view of a steerable apparatus in accordance with a preferred embodiment of a present invention.

As illustrated for example in FIG. 1, a preferred implementation of a present invention is a steerable device 10 having a handle 12 and an elongate, hollow body 14. In the preferred implementation, the elongate body 14 is a sheath having a lumen through which a catheter having diagnostic and/or therapeutic element(s) may be advanced.

The exemplary handle 12 consists partially of a handle body 16 and a piston 18. The piston 18, which is slidably mounted in a longitudinally extending aperture in the handle body 16, includes a thumb rest 20. The handle body 16, piston 18 and thumb rest 20 are preferably formed from machined or molded plastic. Other features of the exemplary handle 12 are discussed below in Section IV. In the exemplary embodiment, one end of a steering wire 22 is secured to the distal portion 24 of the elongate body 14. The steering wire 22 passes through the proximal portion 26 of the elongate body 14 to the handle body 16, where the other end is secured. As discussed in Section III below, the elongate body distal portion 24 and proximal portion 26 are joined to one another at a joint 25.

In the illustrated embodiment, the elongate body is secured to, and travels with, the piston 18. As such, when the exemplary piston 18 is moved distally from the position shown in FIG. 1, the steering wire 22 exerts a pulling force on the distal portion 24 of the elongate body 14, thereby causing the distal portion of the elongate body to deflect into a curved orientation.

Other types of steering apparatus may be used in place of the exemplary piston-based configuration. For example, a handle may be provided that includes a rotating cam, to which the steering wire is connected, and a steering lever connected to the rotating cam. Manipulation of the steering lever causes the steering wire to deflect the distal portion of the elongate body. This type of steering apparatus is disclosed in U.S. Pat. No. 5,636,634.

Figure 2:
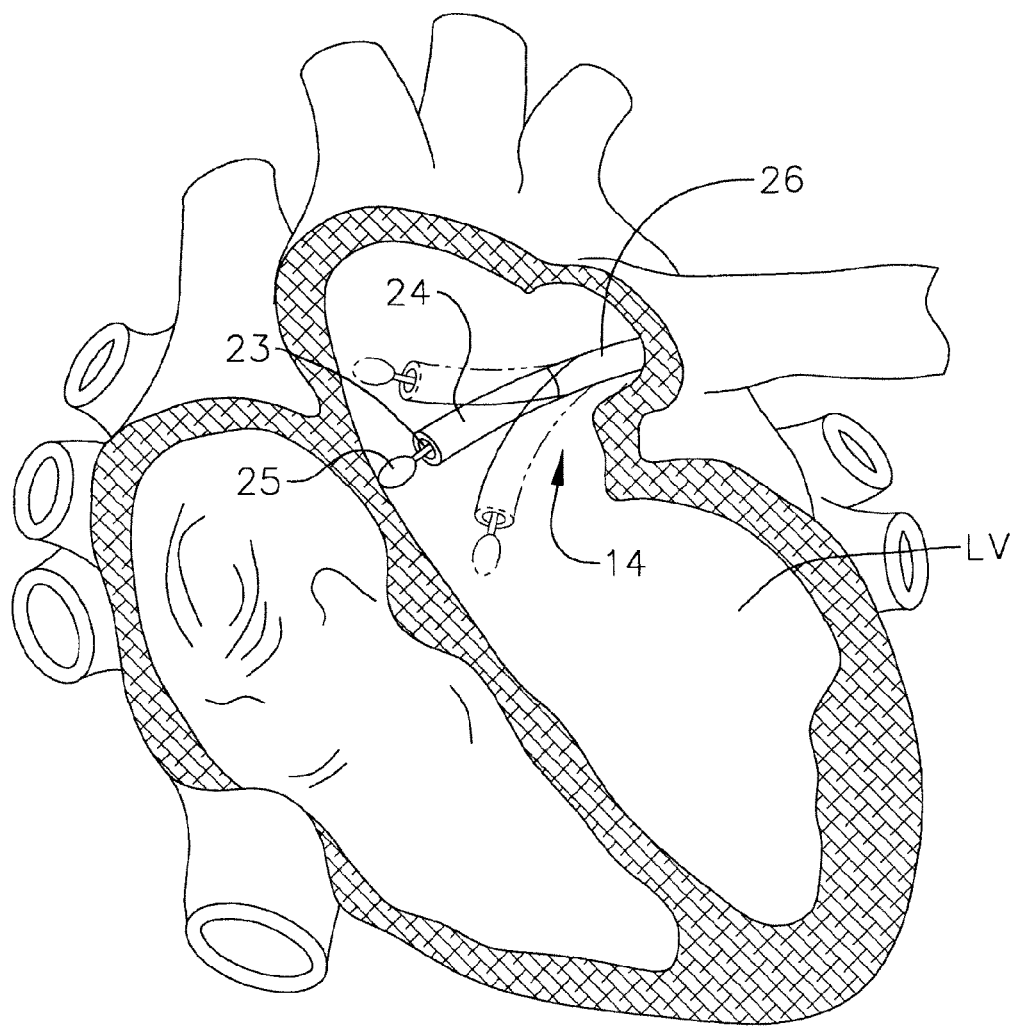
FIG. 2 is a partial section view showing a steerable apparatus in accordance with a preferred embodiment of a present invention, in combination with a catheter carrying a diagnostic or therapeutic element, deployed within the heart.

One exemplary use of the present steerable device is illustrated in FIG. 2. Here, the distal portion 24 of the elongate body 14 has been inserted into the heart and steered into the vicinity of targeted tissue within the left ventricle LV. It should be noted that the heart shown in FIG. 2 is not exactly anatomically correct, and is shown in diagrammatic form to demonstrate the features of the exemplary device. A catheter 23 is extending from the distal portion 24 so that an element 25 (such as a diagnostic and/or therapeutic element) may be positioned adjacent myocardial tissue.

II. Elongate Body Distal Portion

Figure 3:
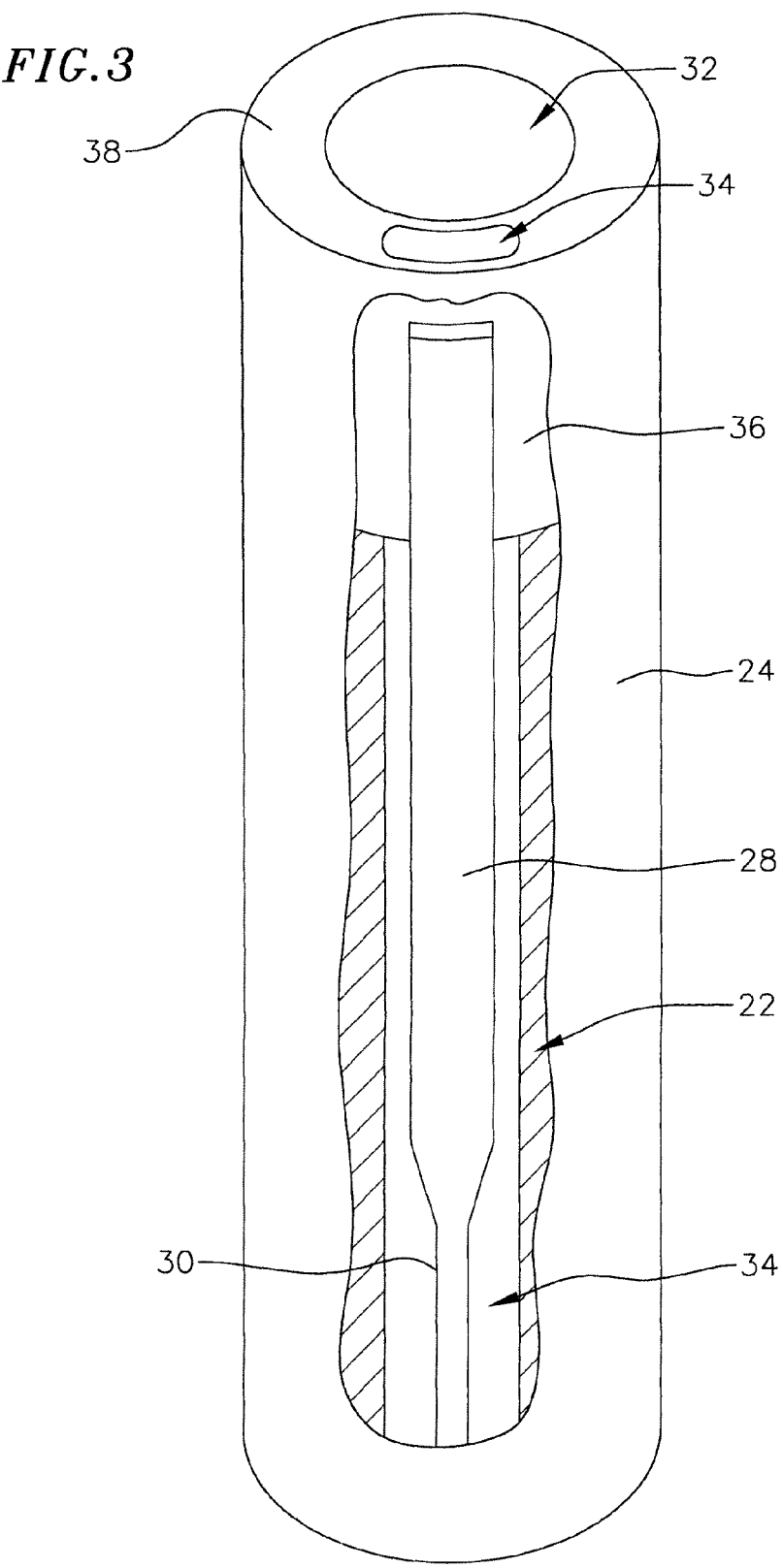
FIG. 3 is a perspective, partial section view of an elongate body distal portion in accordance with a preferred embodiment of a present invention.

In accordance with a preferred embodiment of a present invention, and as illustrated for example in FIG. 3, the portion of the steering wire 22 that is secured to the distal portion 24 of the elongate body 14 has a non-circular cross-section. Although other shapes may be employed, the distal portion 28 of the exemplary steering wire 22 (also referred to as the "non-circular portion") is substantially flat and preferably free of sharp edges that could damage the distal portion 24 of the elongate body 14. A substantially flat steering wire distal portion 28 having a width to thickness ratio between about 1.5 to 1 and about 10 to 1 is preferred. The remainder of the steering wire (referred to herein as the proximal portion 30) has a circular cross-section.

The exemplary elongate body distal portion 24 illustrated in FIG. 3 includes two lumens, a central lumen 32 through which diagnostic and therapeutic apparatus may be advanced and a steering wire lumen 34 in which the steering wire 22 is located. The central lumen 32 preferably terminates at the distal end 38 of the distal portion 24, thereby defining a distal end aperture through which diagnostic or therapeutic elements may exit the elongate body 14. However, the central lumen may also terminate in the side wall of the distal portion 24, thereby defining a side exit aperture. In the illustrated embodiment, the cross-sectional shape of the steering wire lumen 34 corresponds to that of the substantially flat steering wire distal portion 28. This prevents unwanted rotation of the steering wire 22. However, the steering wire lumen 34 may have other cross-sectional shapes, such as an elliptical shape, which will also prevent rotation of a non-circular steering wire or portion thereof.

As shown by way of example in FIG. 3, the steering wire 22 may be secured to an anchoring member 36 that is located within elongate body distal portion 24. The steering wire 22 may be secured to the anchoring member 36 by, for example, welding or adhesive. The exemplary anchoring member 36 is in the form of a cylinder. However, other shapes, such as an annular disk shape, could be used should they be required by a particular application. The anchoring member 36 provides a relatively long attachment surface, thereby decreasing the likelihood that the steering wire 22 will become disconnected from the elongate body distal portion 24. In addition, the anchoring member 36 may be formed from radiopaque material such as platinum or gold plated stainless steel. The radiopacity allows the distal portion of the elongate body to be observed by the physician using conventional fluoroscopic techniques. Other materials include rigid polymer and ceramic materials that are compounded with radiopaque material.

There are a number of advantages associated with the preferred embodiment illustrated in FIGS. 1-3. For example, when the distal portion 24 of the elongate body 14 is deflected from the orientation shown in FIG. 4a to the orientation shown in FIG. 4b, the steering wire will exert a force F along the elongate body distal portion. In conventional devices employing pull wires having a circular cross-section, the distal portion wall must be relatively thick in order to prevent the steering wire from tearing through the wall of the sheath or other elongate body. The wall in preferred embodiment illustrated in FIGS. 1-3 may be made thinner than conventional devices formed from the same material because the exemplary substantially flat (or otherwise non-circular) steering wire distal portion 28 distributes the force F over a greater surface area than does a steering wire having a circular cross-section.

The use of the present non-circular steering wire also prevents out of plane bending. In other words, when bending force is applied to the elongate body distal portion 24, it will bend about an axis that is both perpendicular to the longitudinal axis of the elongate body and parallel to the width dimension of the steering wire non-circular portion 28. The steering wire non-circular portion 28 also provides a larger surface area for attaching the steering wire to the exemplary anchoring member 36 (or other portion of the elongate body) than does a circular wire.

One utilization of the present invention is a steerable sheath that may be used in cardiac treatments such as percutaneous myocardial revascularization (PMR). In a preferred embodiment, the outer diameter of the elongate body 14 is about 0.118 inch and the diameter of the central lumen 32 is about 0.075 inch. The distal portion 24 of the elongate body is about 1.4 inches in length and should be flexible enough to bend approximately 135° (note that a 90° bend is shown in FIG. 4*b*), yet have sufficient memory to return to its original orientation when bending forces are removed. To provide the necessary flexibility, the distal portion 24 of the elongate body may be formed from a relatively flexible material through a dual lumen extrusion process. Preferred relatively flexible materials include, for example, fluoropolymers such as THV 200, a commercially available combination of tetrafluoroethylene, hexafluoropropylene and vinylidene fluoride, and Pellethane 80A. Radiopaque material, such as barrium, bismuth, and tungsten may be combined with the flexible material for visualization purposes.

In the exemplary steerable sheath that may be used in PMR and other cardiac care procedures, the anchoring member 36 is preferably about 0.100 inch in length and has a wall thickness of about 0.002 inch. The diameter of the circular proximal portion 30 of the steering wire 22 is about 0.009 inch, while the width of the non-circular portion 28 ranges from about 0.012 inch to about 0.017 inch and the thickness ranges from about 0.003 inch to about 0.005 inch. To accommodate the non-circular portion 28, the steering wire lumen 34 has a shape corresponding to that of the non-circular portion and cross-sectional dimensions which are about 0.001 inch to about 0.003 inch larger than those of the circular portion. The length of the steering wire non-circular portion 28 is preferably slightly less than that of the elongate body distal portion 24. As a result, only the circular proximal portion 30 of the steering wire 22 will pass through the circular steering wire lumen in the elongate body proximal portion 26 (discussed in Section III), even when the distal portion 24 is being bent. Alternatively, the non-circular portion 28 will extend the entire length of the elongate body distal portion 24 and the steering wire lumen in the elongate body proximal portion 26 will be modified accordingly.

Turning to FIG. 5, the steering wire 22 may be secured to the anchoring member 36 prior to the insertion of both into the elongate body distal portion 24. The combined steering wire/anchoring member assembly may be inserted into the elongate body distal portion 24 as follows. The elongate body distal portion 24 is heated to its softening temperature. The proximal end of the steering wire 22 is then inserted into the steering wire lumen 34. The anchoring member 36 is moved toward the elongate body distal portion 24 until it reaches the distal end 38 of the distal portion. The anchoring member 36 is then forced through the distal end 38 of the softened distal portion 24 to the position shown in FIG. 3. The distal end of the steering wire lumen 34 will not be present after the softened distal portion 24 hardens. Additionally, in order to insure that the anchoring member 36 will not tear through the distal end 38, a relatively thin annular piece of distal portion material can be molded onto the distal end.

A stiffening member (or "spine") may be provided in order to prevent compression (or "buckling") of the elongate body distal portion 24 during bending, which can sometimes happen in those instances where the distal portion is formed with very thin walls or from very flexible material. The stiffening member may also be used to return the elongate body distal portion 24 to a neutral position after a steering operation, influence the curvature during steering, provide a pre-bend in a direction other than the direction in which the distal portion is bent during steering, and to increase the torque transmission properties of the distal portion. A variety of stiffening members are illustrated in FIGS. 6*a*-10*b*. They may be used in combination with steerable devices including steering wires having cross-sections that are circular, non-circular or some combination thereof.

Figure 6A:
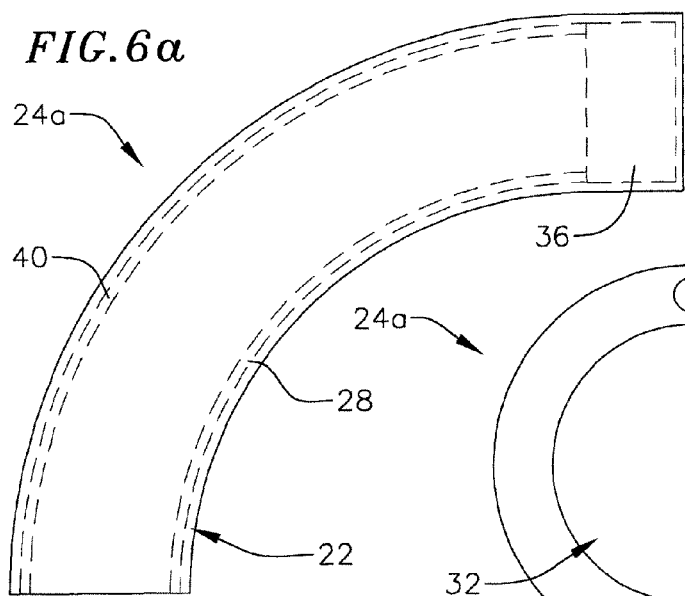
FIG. 6a is side view of an elongate body distal portion in accordance with another preferred embodiment of a present invention.
Figure 6B:
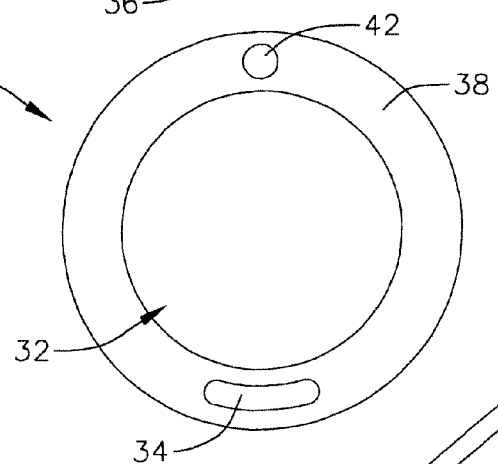

As shown by way of example in FIGS. 6*a* and 6*b*, an elongate body distal portion 24*a* includes a stiffening member 40 located in a stiffening member lumen 42. The stiffening member lumen 42 is itself located on the side of the elongate body distal portion 24*a* opposite the steering wire 22 (and steering wire lumen 34). The stiffening member 40, which may be circular in cross-section (as shown in FIGS. 6*a* and 6*b*) or non-circular in cross-section, is bonded or otherwise secured in place.

Figure 6C:
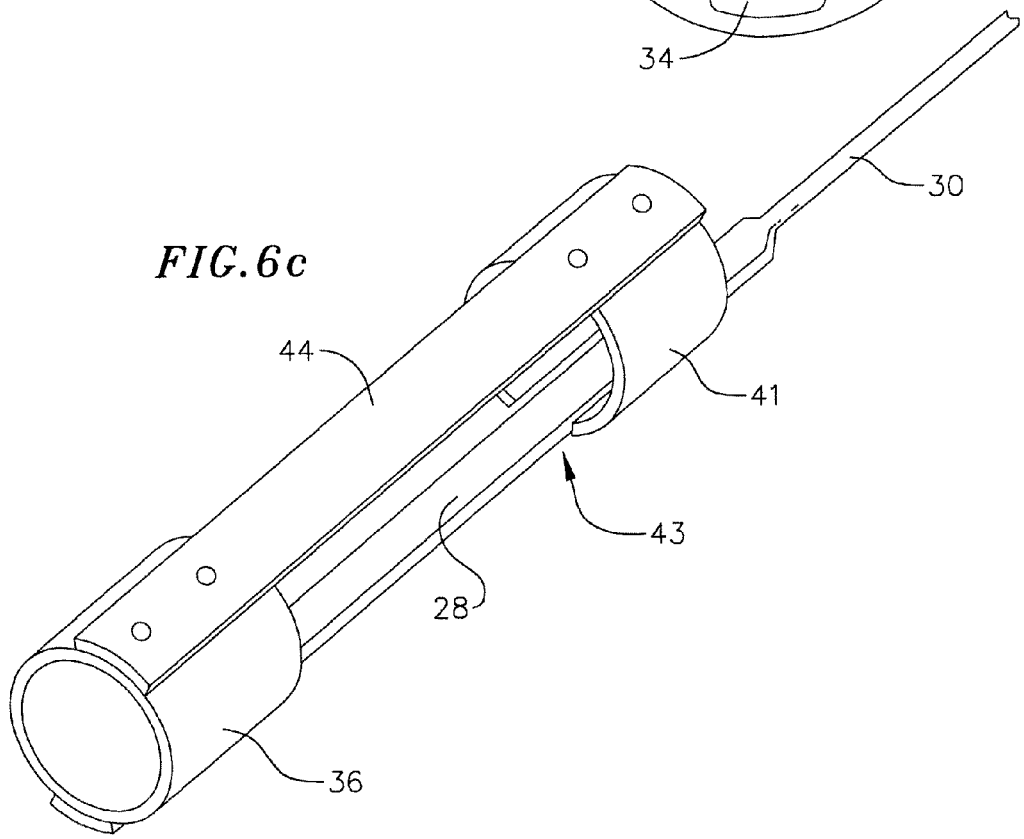
FIG. 6c is a perspective view of a stiffening member, steering wire and anchoring member assembly in accordance with a preferred embodiment of a present invention.

Alternatively, the stiffening member may be secured to the anchoring member 36. Referring to FIG. 6*c*, the distal end of a stiffening member, such as stiffening member 44 (described below), may be secured to the anchoring member 36 and an anti-tear device 41 may be secured to the proximal end of the stiffening member. The anti-tear device 41, which is located within the elongate body distal portion 24*a* and which includes a slot 43 through which the steering wire distal portion 28 passes, spreads the forces associated with the bending of the stiffening member 44 over a greater surface area, thereby preventing the bending member from tearing through the elongate body distal portion. In other words, the anti-tear device 41 performs the function of increasing the surface area of the elongate body distal portion 24*a* over which the force is applied when the stiffening member 44 is bent to prevent the stiffening member from tearing through the elongate body. A suitable anti-tear device may be constructed by forming the slot 43 in a hypotube.

In another alternative arrangement, the stiffening member 44 and anti-tear device 41 may be replaced by a second steering wire 22 located on the opposite side as the first steering wire. While one of the steering wires is used for steering purposes, the other steering wire will act as a stiffening member.

Referring to FIGS. 7*a* and 7*b*, another elongate body distal portion (here identified by reference numeral 24*b*) includes a pair of stiffening members 40 respectively located in a pair of stiffening member lumens 42. Although other configurations may be employed, the stiffening member lumens 42 in this embodiment are located 90° from the steering wire lumen 34 and 180° from one another.

Figure 8D:
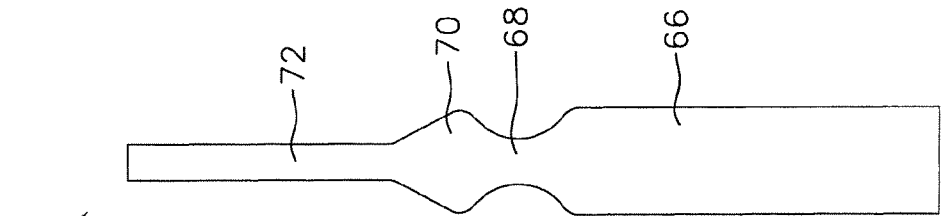
FIGS. 8a, 8b, 8c and 8d are front elevation views of stiffening members in accordance with preferred embodiments of a present invention.
Figure 8C:
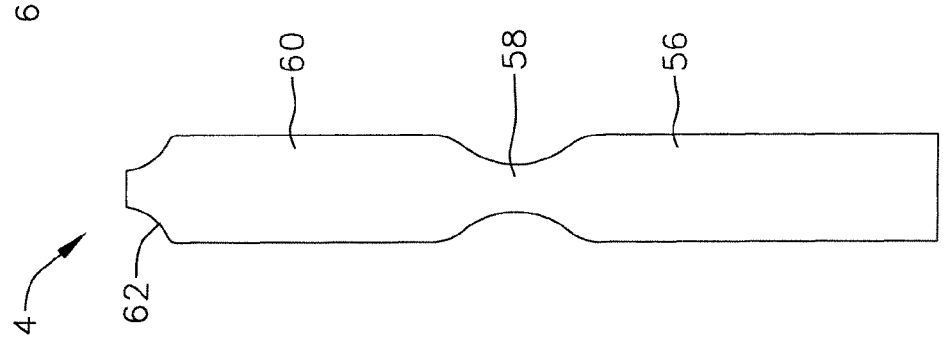
Figure 8B:
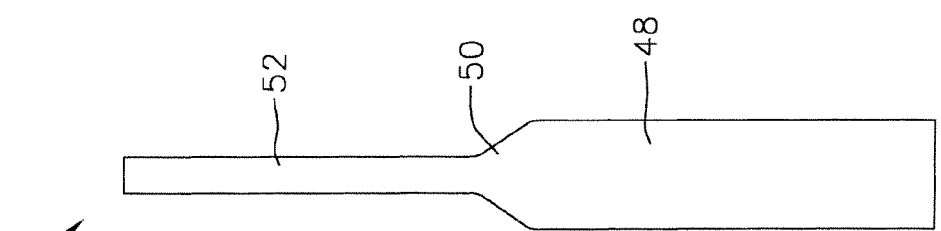
Figure 8A:
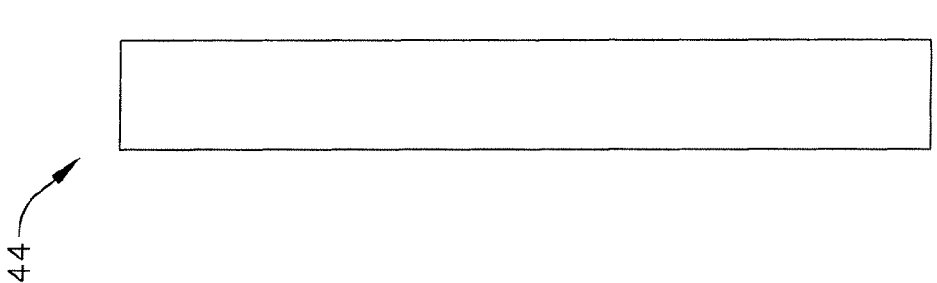
Figure 9:
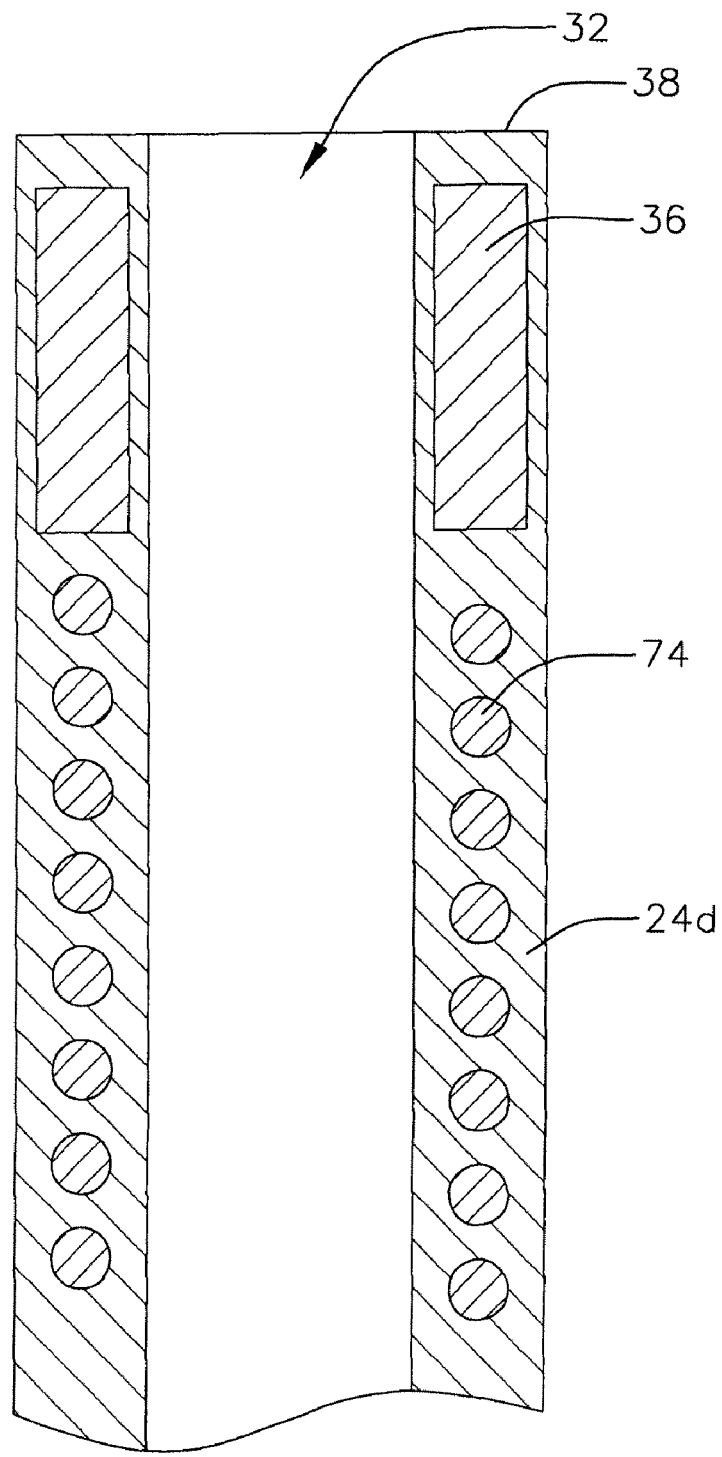
FIG. 9 is partial side section view of an elongate body distal portion in accordance with yet another preferred embodiment of a present invention.
Figure 18:
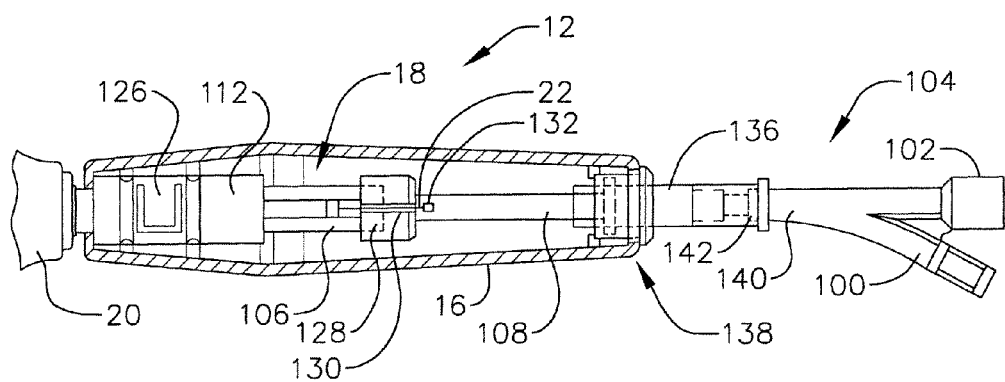
FIG. 18 is a partial cutaway view of the exemplary handle illustrated in FIG. 1.
Figure 19:
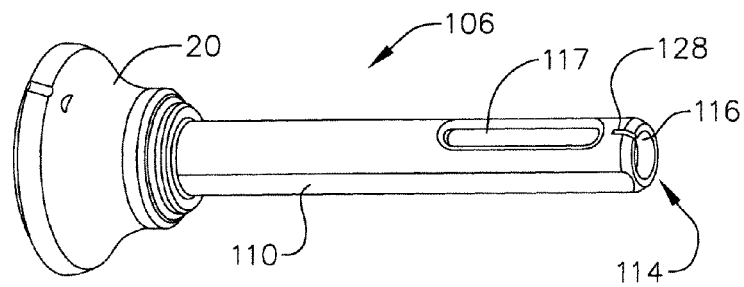
FIG. 19 is a perspective view of a portion of the exemplary handle illustrated in FIGS. 1 and 18.
Figure 20:
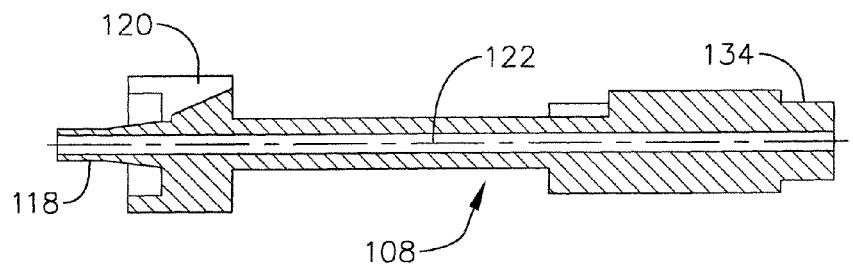
FIG. 20 is side partial section view of another portion of the exemplary handle illustrated in FIGS. 1 and 18.

A number of exemplary stiffening members with rectangular cross-sections are illustrated in FIGS. 8*a*-8*d* and arranged such that the proximal end is the bottom end in the FIGURES. Referring first to FIG. 8*a*, stiffening member 44 has a constant width from one longitudinal end to the other. The stiffening member illustrated in FIG. 8*b*, which is generally represented by reference numeral 46, includes a relatively wide proximal portion 48, a narrowing transition portion 50 and a relatively narrow distal portion 52. Stiffening member 46 will produce a bend in the elongate body distal portion 24*c* (FIG. 8*e*) with a smaller radius curve than the stiffening member 44 illustrated in FIG. 8*a*. Stiffening member 54 (FIG. 8*c*) includes a relatively wide proximal portion 56, a relatively narrow notch portion 58, a relatively wide distal portion 60 and a tapered portion 62. As compared to the bend produced by the stiffening member 44 illustrated in FIG.

8a, the bend produced by the stiffening member 54 will be localized in the area of notch portion 58. Turning to FIG. 8d, stiffening member 64 includes a relatively wide proximal portion 66, a relatively narrow notch portion 68, a relatively wide middle portion 70 and a relatively narrow distal portion 72. Stiffening member 64 will produce a bend in the elongate body distal portion that has a smaller radius in the area of distal portion 72 and the same radius in the area of proximal portion 66, as compared to the stiffening member 44 illustrated in FIG. 8a.

The stiffening members illustrated in FIGS. 8a-8d may be employed in steerable devices having stiffening member lumens with generally rectangular shapes. As illustrated for example in FIG. 8e, elongate body distal portion 24c includes a stiffening member lumen 25 and a circular steering wire lumen 27 for a steering wire 29 with a circular cross-section. Of course, a steering wire with a non-circular cross-section may also be employed. The stiffening members may be bonded or otherwise secured in place or secured to the anchoring member 36.

The stiffening members illustrated in FIGS. 8a-d are about 0.5 inch to about 6.0 inches in length. The width of the relatively wide portions is about 0.010 inch to about 0.050 inch and the width of the relatively narrow portions is about 0.003 inch to about 0.030 inch. The thickness of the exemplary stiffening members is constant and about 0.003 inch to about 0.009 inch.

The stiffening members may also be prebent in one or more locations by heat setting or other metal or plastic forming techniques. As illustrated for example in FIG. 8f, stiffening member 54 may be formed with a single approximately 90° bend. The prebent stiffening member may be arranged such that it causes the elongate body distal portion 24c to bend in a direction opposite to the steering direction, thereby providing the elongate body with two-directional steering capabilities.

As shown by way of example in FIGS. 8g-l, the width of a stiffening member may be constant, and the thickness of a particular region, or a plurality of regions, may be increased or decreased as desired to alter the bending characteristics of the stiffening member. Turning first to FIGS. 8g and 8h, a stiffening member 45 has a thickness that decreases from the proximal end to the distal end, which results in a bending radius that decreases from the proximal end to the distal end. In an exemplary implementation, the width of the stiffening member 45 is about 0.017 inch and the thickness decreases from about 0.012 inch to about 0.004 inch. The exemplary stiffening member 47 illustrated in FIGS. 8i and 8j includes a central member 49 with a constant thickness and a base member having a relatively thin portion 51 and a relatively thick portion 53. Such a stiffening member will have two distinct bending radii, with the distal bending radius being smaller than the proximal bending radius. In an exemplary implementation, the width of the stiffening member 47 is about 0.017 inch, the width of the central member 49 is about 0.005 inch, the thickness of the central member is about 0.009 inch, the thickness of the relatively thin portion is about 0.004 inch and the thickness of the relatively thick portion is about 0.007 inch. Turning to FIGS. 8k and 8l, an exemplary stiffening member 55 includes a base member 57 with a relatively constant thickness and a central member 59 having relatively thick portions 61 and 63 and a relatively thin portion 65 therebetween. The stiffening member 55 has a variable bending radius that transitions slowly from relatively large to relatively small to relatively large. In an exemplary implementation, the width of the stiffening member 55 is about 0.017 inch, the width of the central member 59 is about 0.005 inch, the thickness of the base member is about 0.004 inch, and the thickness of the central member varies from about 0.009 inch to about 0.005 inch.

A coil-type stiffening member may also be used to maintain the cross-sectional shape of the elongate body distal portion 24, which is circular in the illustrated embodiments, and to bring the distal portion back to the neutral position after a steering operation. As illustrated for example in FIG. 9, an elongate body distal portion 24d includes a coil 74 embedded therein to help maintain the circular shape of the distal portion. Of course, the coil 74 and steering wire lumen 34 (not visible in FIG. 9) must be radially offset from one another within the distal portion 24d. In an alternate configuration (not shown), the anchoring member 36 is removed, the coil 74 is extended into the region occupied by the anchoring member, and the steering wire is secured to the distal end of the coil.

Another coil-type stiffening member, which is generally represented by reference numeral 76, is illustrated in FIG. 10a. Stiffening member 76 includes a generally rectangular portion 78 and a coil portion 80 which are preferably spot welded, soldered or otherwise connected to one another. Both portions are preferably rectangular in cross-section, but may also be circular. A steering wire 82 is secured to the distal end of the coil portion 80. Although a steering wire with a circular cross-section is shown in FIG. 10a, a steering wire with a non-circular portion may also be used. Turning to FIG. 10b, a stiffening member similar to that illustrated in FIG. 10a may be formed from a hypotube 84 having a plurality of slots 86 formed therein by laser cutting, electrostatic discharge machining, and chemical etching.

The various stiffening members described above may be formed from a variety of metals and plastics such as Nitinol material, 17-7 steel, a nickel/cobalt/chromium allow sold under the trade name Elgiloy®, resilient plastics, and metal/plastic composites.

Elongate body distal portions may also be constructed in such a manner that they bend as if they included a stiffening member despite the fact that no stiffening member is included. Such an arrangement allows for a reduction in wall thickness, thereby enabling a greater ID for a given OD. Referring first to FIGS. 11a-11c, an exemplary distal portion 24e includes a relatively soft, flexible front member 67 and a relatively hard, less flexible rear member 69. The steering wire 28 is located within the front member 67. The rear member 69, which should be more flexible than the proximal portion 26, acts as a spine to prevent compression of the area of the elongate body distal portion 24e opposite the steering wire 28. The elongate body distal portions illustrated in FIGS. 12-14 also include steering wires located in their respective relatively soft, flexible areas and relatively hard, less flexible areas opposite the steering wire that act as spines. The differences in hardness and flexibility may be accomplished by forming the respective areas (or members) from the same type of material (e.g. Pellethane), albeit with different durometer values, or by using a different type of material for each area.

The front and rear members 67 and 69 are semicircular in cross-section and each occupies a portion (or segment) of the perimeter that is of constant size (about 180° each) from one longitudinal end of the elongate body distal portion to the other. Such a shape produces the bending characteristics illustrated in FIG. 11a. The bending characteristic may be changed, however, by varying the sizes of the perimeter segments occupied by the front and rear members over the length of the distal portion.

As illustrated for example in FIG. 12, the respective segments of the perimeter occupied by the relatively soft, flexible front member 71 and the relatively hard, less flexible rear member 73 in the distal portion 24f vary in size from essentially none (about 0°) to essentially all (about 360°). At the distal end, the front member 71 occupies essentially all of the perimeter and the rear member 73 occupies essentially none of the perimeter. Moving proximally, the size of the segment occupied by the front member 71 gradually decreases, while the size of the segment occupied by the rear member 73 gradually increases, until the front member occupies essentially none of the perimeter and the rear member occupies essentially all of the perimeter, and so on back and forth in the manner illustrated in FIG. 12. Such an arrangement results in a relatively elliptical bend.

Turning to FIG. 13, the size of the segment of the perimeter occupied by the relatively soft, flexible front member 75 in the distal portion 24g varies from essentially all at the distal end of the distal portion to essentially none at the proximal end. Conversely, the size of the segment of the perimeter occupied by the relatively hard, less flexible rear member 77 increases from essentially none at the distal end of the distal portion 24g to essentially all at the proximal end. Such an arrangement results in a bending radius that decreases from the proximal end to the distal end.

The number of members with different flexibilities may also be varied. As illustrated in FIG. 14, distal portion 24h includes a relatively soft, flexible front member 79, a relatively hard, less flexible rear member 81 and an intermediate member 83 therebetween. The hardness and flexibility of the intermediate member 83 is between that of the front and rear members 79 and 81. Here, the steering wire 28 will be located on right side (as shown in FIG. 14), which is more flexible than the opposite side at any point along its length.

It should also be noted that the relatively hard, less flexible rear members described above may be pre-bent in a direction opposite to the steering direction, thereby providing the elongate body with two-directional steering capabilities in a manner similar to that described above with reference to FIG. 8f.

Turning to the exemplary embodiment illustrated in FIGS. 15a and 15b, elongate body distal portion 24i includes a relatively soft, flexible member 85 and one or more relatively hard, less flexible members 87. The relatively hard, less flexible members 87 keep the bending of the distal portion in plane and prevent the distal portion from compressing during steering in a manner similar to the stiffening members illustrated in FIGS. 6a-7b. Here too, the differences in hardness and flexibility may be accomplished by forming the respective areas (or members) from the same type of material, albeit with different durometer values, or from different types of material.

Finally, the bending characteristics of an elongate body distal portion may also be adjusted by having two or more sections with different flexibilities. As illustrated for example in FIG. 16, an elongate body distal portion 24j includes sections 89, 91 and 93 that progressively decrease in hardness and flexibility, thereby producing a distal portion with a bending radius that progressively decreases from the proximal end to the distal end. Such an arrangement will not, however, produce the stiffening member-like effects similar to the embodiments illustrated in FIGS. 11a-15b. Each of the sections 89, 91 and 93 should be more flexible than the proximal portion 26 and the relative positions of the sections (as well as the number thereof) may be varied as desired to create the desired bending characteristics.

III. Elongate Body Proximal Portion

As illustrated for example in FIG. 17, the exemplary elongate body proximal portion 26 includes an inner portion 88 through which a central lumen 90 extends, a reinforcing element 92, and an outer portion 94. The reinforcing element 92 increases the torque transmission properties of the proximal portion 26 and also increases its stiffness. The outer portion 94 includes a steering wire lumen 96 (note steering wire 22) which may be coated with a lubricious material 98 such as Teflon®. Although other material and structures may be used, the preferred reinforcing element is braided stainless steel having a braid pattern and pick number suitable for the intended application. Exemplary alternative reinforcing elements include double helix structures and three-dimensional braids. Reinforcing elements, braided or not, may also be formed, for example, from Nylon® and other polymer materials.

The steering wire lumen 96 in the proximal portion 26 of the elongate body 14 is aligned with the steering wire lumen 34 in the distal portion 24. However, in contrast to the steering wire lumen 34, the steering wire lumen 96 is preferably circular in cross-section. In those embodiments where the length of the non-circular portion 28 of the steering wire 22 is less than the length of the elongate body distal portion 24, the steering wire lumen 96 in the proximal member may be circular in cross-section all the way to the distal end thereof. In other embodiments, where the steering wire non-circular portion 28 extends to the proximal end of the elongate body distal portion 24, the steering wire lumen 96 may be either non-circular in its entirety, or simply have a distal end that is chamfered into a funnel shape to accommodate the non-circular portion.

As noted in Section II, one implementation of the present invention is a steerable sheath that may be used in cardiac treatments such as PMR. Here, like the elongate body distal portion 24, the proximal portion 26 has an outer diameter of about 0.118 inch and the central lumen 90 (which is aligned with the central lumen 32 in the distal portion) has a diameter of 0.075 inch. The length of the proximal portion 26 in this implementation may be about 7 inches to about 70 inches. Also, a strain relief element (not shown) may be located over the proximal portion 26 near the thumb rest 20.

The proximal portion 26 may be formed by first extruding the inner portion 88 over a mandrel. The reinforcing element 92 is then placed over the inner portion 88. Next, the outer portion 94, including the steering wire lumen 96, is formed in a second extrusion. In those instances where the surface of the steering wire lumen 96 includes the coating of lubricious material 98, that coating is also formed during the second extrusion.

The distal and proximal portions 24 and 26 of the elongate body 14 are secured to one another at the joint 25. The joint may be formed in a variety of ways. For example, an adhesive or thermal butt bonding technique may be used. However, the preferred method is an overlapping thermal bond. Specifically, the distal and proximal portions 24 and 26 are arranged such that a small length of the distal portion overlaps the proximal portion (or vice versa). Heat is then applied to the overlapping region, which causes the overlapping portions to bond to one another.

The inner and outer portions 88 and 96 are both preferably formed from THV 200, which is fairly lubricious. Here, the lubricious coating 98 is not required. In other embodiments, the inner portion 88 is formed from a polyether block amide such as PEBAX®, which bonds well with an elongate body distal portion 24 that is formed from Pellethane, and the outer portion 94 is formed from a fluoropolymer such as THV 200. In still other embodiments, the inner portion 88 is formed from a fluoropolymer such as THV 200 and the outer portion 94 is formed from a polyether block emide such as PEBAX®. The lubricious coating 98 is especially useful here.

IV. Handle

An exemplary handle that may be used in conjunction with the elongate body 14 is the handle 12 illustrated in FIGS. 1 and 18-20. Similar handles are commonly found in steerable catheters manufactured by EP Technologies, Inc. under the trade name Polaris®, with one important exception. The piston 18 in the present handle 12 includes a lumen that connects the central lumen in the elongate body 14 to an input port 100 and a homeostasis valve 102. In the illustrated embodiment, the input port 100 and hemostasis valve 102 are part of a Y-adapter 104 that is capable of rotating 360°.

The exemplary piston 18 is a two-part assembly composed of a forward piston member 106 and a rear piston member 108. The forward piston member 106 includes a main body 110 which supports a portion of the thumb rest 20 at its distal end. The main body 110 extends into the handle body 16 through a piston supporting cylinder 112. The piston supporting cylinder 112 has o-rings at its longitudinal ends that center the main body 110. As shown by way of example in FIG. 13, a lumen 114 extends through the main body 110 and terminates at a frusto-conical surface 116. The proximal portion 26 of the elongate member 14 extends through the lumen 114 and outer surface of the proximal end of the elongate body is bonded to the conical surface 116. A key way 117, which mates with a protrusion on the inner surface of the handle, prevents the piston from rotating.

The exemplary rear piston member 108 includes a conical tip 118 that mates with the conical surface 116 (and distal end of the elongate body 14) and a cap 120 that fits over the forward member main body 110. The rear piston member 108 also includes a lumen 122 which feeds into the Y-adapter 104. To that end, the end 134 of the rear piston member 108 is inserted into the cylindrical portion 136 of the Y-adapter 104 and the two are sealed in a rear sealing assembly 138. The adapter stem 140 rotates relative to the cylindrical portion 136 and an o-ring 142 is provided to create a seal.

The level of friction between the piston 18 and handle body 16 may be controlled in part by a set screw 124 (FIG. 1) that imparts a force onto a tab 126 on the piston supporting cylinder 112.

Turning to the steering wire 22 and the manner in which it may be secured within the handle 12, the main body 110 of the exemplary forward piston member 108 includes a slot 128. The rear piston member cap 120 includes a corresponding slot 130. The steering wire 22 passes through the slots 128 and 130 and bends away from the central axis of the handle body 16. The distal end of the steering wire 22 is secured to an anchor 132 that is itself secured to the handle by a hollow nut and bolt assembly located on the half of the handle body 16 that is not shown in FIG. 18. Steering wire tension is set by rotating the bolt relative to the nut.

Although the present inventions have been described in terms of the preferred embodiments above, numerous modifications and/or additions to the above-described preferred embodiments would be readily apparent to one skilled in the art. It is intended that the scope of the present inventions extends to all such modifications and/or additions.

We claim:

1. An apparatus, comprising:
   an elongate body defining a proximal portion and a distal portion and including a wall defining an inner surface, an outer surface and a lumen extending from the proximal portion to an aperture in the distal portion;
   a steering wire having a distal portion;
   an anchoring member associated with the distal portion of the elongate body, configured such that it does not obstruct the aperture in the distal portion of the elongate body, and directly secured to the steering wire;
   means, directly connected to the anchoring member, for preventing compression of the elongate body distal portion during bending of the elongate body distal portion; and
   a tubular member, that is a partial circle in cross-section and includes first and second longitudinally extending edges that together define a slot, which extends completely through the tubular member at the first and second edges, in which a portion of the steering wire is located, positioned relative to the means for preventing compression so as to prevent the means for preventing compression from tearing through the elongate body when the means for preventing compression bends.

2. An apparatus as claimed in claim 1, wherein at least a portion of the steering wire is located within the elongate body wall between the inner surface and the outer surface.

3. An apparatus as claimed in claim 1, wherein the anchoring member is located within the elongate body wall between the inner surface and the outer surface.

4. An apparatus as claimed in claim 3, wherein the means for preventing compression is located within the elongate body wall between the inner surface and the outer surface.

5. An apparatus as claimed in claim 1, wherein the means for preventing compression is located within the elongate body wall between the inner surface and the outer surface.

6. An apparatus as claimed in claim 1, wherein
   the elongate body defines a longitudinal axis;
   the steering wire and the means for preventing compression are radially offset from the longitudinal axis; and
   the steering wire and the means for preventing compression are substantially diametrically opposed from one another.

7. An apparatus as claimed in claim 1, wherein the tubular member defines proximal and distal longitudinal ends and the first and second longitudinally extending edges extend continuously from the proximal longitudinal end to the distal longitudinal end.

8. An apparatus as claimed in claim 7, wherein the portion of the steering wire that is located within the slot is axially and radially aligned with the slot.

9. An apparatus, comprising:
   an elongate body defining a diameter, a proximal portion and a distal portion and including a wall defining an inner surface, an outer surface and a lumen extending from the proximal portion to an aperture in the distal portion;
   a stiffening member associated with the distal portion of the elongate body and defining a proximal end, a distal end, a length that extends from the proximal end to the distal end, a proximal half that occupies one-half of the length and a distal half that occupies one-half of the length;
   a tubular anti-tear device positioned within the elongate body wall between the inner surface and the outer surface adjacent to at least a portion of the proximal half of the stiffening member and not adjacent to the distal half of the stiffening member, and configured to prevent the stiffening member from tearing through the elongate body when the stiffening member bends; and
   a steering wire, which is not connected to the tubular anti-tear device and which is not located within the stiffening member, having a distal portion operably connected to the distal portion of the elongate body;

wherein the stiffening member and the distal portion of the steering wire are substantially diametrically opposed from one another.

10. An apparatus as claimed in claim 9, wherein the tubular anti-tear device is secured to the stiffening member.

11. An apparatus as claimed in claim 9, wherein the tubular anti-tear device includes a slot.

12. An apparatus as claimed in claim 9, wherein the elongate body defines a longitudinal axis and the stiffening member extends less than entirely around the longitudinal axis.

13. An apparatus as claimed in claim 12, wherein the tubular anti-tear device extends further around the longitudinal axis than the stiffening member.

14. An apparatus as claimed in claim 9, wherein the distal portion of the steering wire is secured to the elongate body at a location within the wall between the inner surface and the outer surface.

15. An apparatus as claimed in claim 9, wherein the stiffening member is located within the elongate body wall between the inner surface and the outer surface.

16. An apparatus as claimed in claim 9, wherein there is no an anti-tear device positioned adjacent to the distal half of the stiffening member.

17. An apparatus, comprising:
an elongate body defining a proximal portion and a distal portion defining a circumference and including a wall defining an inner surface, an outer surface and a lumen extending from the proximal portion to an aperture in the distal portion;
a steering wire having a distal portion operably connected to the distal portion of the elongate body;
a stiffening member associated with the distal portion of the elongate body; and
a substantially c-shaped anti-tear device, including first and second longitudinally extending edges that together define a slot which extends completely through the tubular member at the first and second edges, associated with the stiffening member such that a portion of the stiffening member is distal of the anti-tear device;
wherein a portion of the steering wire is positioned within the slot; and
wherein the stiffening member is substantially longer than the anti-tear device and is coextensive with substantially less than one-half of the circumference.

18. An apparatus as claimed in claim 17, wherein at least a portion of the steering wire is located within the elongate body wall between the inner surface and the outer surface.

19. An apparatus as claimed in claim 17, wherein the stiffening member is located within the elongate body wall between the inner surface and the outer surface.

20. An apparatus as claimed in claim 17, wherein the substantially c-shaped anti-tear device is located within the elongate body wall between the inner surface and the outer surface.

21. An apparatus as claimed in claim 17, wherein
the elongate body defines a longitudinal axis;
the steering wire and the stiffening member are radially offset from the longitudinal axis; and
the steering wire and the stiffening member are substantially diametrically opposed from one another.

22. An apparatus as claimed in claim 17, wherein the anti-tear device defines proximal and distal longitudinal ends and the first and second longitudinally extending edges extend continuously from the proximal longitudinal end to the distal longitudinal end.

23. An apparatus as claimed in claim 22, wherein the portion of the steering wire that is located within the slot is axially and radially aligned with the slot.

24. An apparatus, comprising:
an elongate body defining a proximal portion, a distal portion and a diameter, the distal portion defining a longitudinal axis, and including a wall defining an inner surface, an outer surface and a lumen extending from the proximal portion to an aperture in the distal portion;
a stiffening member, defining a proximal portion and a distal portion, associated with the distal portion of the elongate body such that the stiffening member will apply a force over an elongate body surface area when the stiffening member is bent;
anti-tear means, secured directly to the proximal portion of the stiffening member and located within the elongate body wall between the inner surface and the outer surface, for preventing the stiffening member from tearing through the outer surface of the elongate body wall by increasing the elongate body surface area over which the force is applied when the stiffening member is bent; and
a steering wire, which is not connected to the anti-tear means, having a distal portion operably connected to the distal portion of the elongate body;
wherein the stiffening member and the distal portion of the steering wire are offset from one another by about 180 degrees about the longitudinal axis.

25. An apparatus as claimed in claim 24, wherein at least a portion of the steering wire is located within the elongate body wall between the inner surface and the outer surface.

26. An apparatus as claimed in claim 24, wherein the stiffening member is located within the elongate body wall between the inner surface and the outer surface.

27. An apparatus, comprising:
an elongate body defining a longitudinal axis, a proximal portion and a distal portion and including a substantially solid single-piece wall defining an inner surface, an outer surface and a lumen extending from the proximal portion to an aperture in the distal portion;
a steering wire having a distal portion;
an anchoring member located within the distal portion of the substantially solid single-piece elongate body wall between the inner surface and the outer surface and secured to the steering wire;
a stiffening member associated with the distal portion of the elongate body and defining a distal end, the distal end of the stiffening member being directly secured to the anchoring member; and
a substantially tubular member directly secured to the stiffening member and defining a continuous length in a direction parallel to the longitudinal axis and a wall thickness, the continuous length being substantially greater than the wall thickness;
wherein the steering wire is not connected to the substantially tubular member: and
wherein the elongate body and the substantially tubular member are separate elements.

28. An apparatus as claimed in claim 27, further comprising:
a handle, operably connected to the elongate body and to the steering wire, adapted pull the steering wire relative to the elongate body.

29. An apparatus as claimed in claim 27, wherein the steering wire extends to the proximal portion of the elongate body and is movable relative to the proximal portion of the elongate body.

30. An apparatus as claimed in claim 27, wherein the anchoring member is directly secured to the steering wire.

31. An apparatus as claimed in claim 27, wherein the substantially tubular member is located within the distal portion of the substantially solid elongate body wall between the inner surface and the outer surface.

32. An apparatus as claimed in claim 27, wherein the single-piece wall extends from the inner surface to the outer surface.

33. An apparatus, comprising:
- an elongate body defining a longitudinal axis, a proximal portion and a distal portion and including a substantially solid single-piece wall defining an inner surface, an outer surface and a lumen extending from the proximal portion to an aperture in the distal portion;
- a steering wire having a distal portion;
- an anchoring member located within the distal portion of the substantially solid single-piece elongate body wall between the inner surface and the outer surface and secured to the steering wire;
- a stiffening member associated with the distal portion of the elongate body and defining a distal end, the distal end of the stiffening member being directly secured to the anchoring member; and
- a substantially tubular member, including a slot through which the steering wire passes, secured to the stiffening member and defining a continuous length in a direction parallel to the longitudinal axis and a wall thickness, the continuous length being substantially greater than the wall thickness;
- wherein the elongate body and the substantially tubular member are separate elements.

34. An apparatus as claimed in claim 33, wherein the anchoring member is directly secured to the steering wire.

35. An apparatus as claimed in claim 33, wherein the substantially tubular member is directly secured to the stiffening member.

36. An apparatus as claimed in claim 33, wherein the substantially tubular member is located within the distal portion of the substantially solid elongate body wall between the inner surface and the outer surface.

37. An apparatus as claimed in claim 33, wherein the single-piece wall extends from the inner surface to the outer surface.

38. An apparatus, comprising:
- an elongate body defining a longitudinal axis, a proximal portion and a distal portion and including a wall defining an inner surface, an outer surface and a lumen extending from the proximal portion to an aperture in the distal portion;
- a steering wire having a distal portion;
- an anchoring member located within the distal portion of the elongate body wall between the inner surface and the outer surface and secured to the steering wire;
- a stiffening member associated with the distal portion of the elongate body and defining a distal end, the distal end of the stiffening member being directly secured to the anchoring member; and
- a substantially tubular member, which extends less than completely around the longitudinal axis, secured to the stiffening member and defining a continuous length in a direction parallel to the longitudinal axis and a wall thickness, the continuous length being substantially greater than the wall thickness.

39. An apparatus as claimed in claim 38, wherein the anchoring member is directly secured to the steering wire.

40. An apparatus as claimed in claim 38, wherein the substantially tubular member is directly secured to the stiffening member.

41. An apparatus as claimed in claim 38, wherein the substantially tubular member is located within the distal portion of the elongate body wall between the inner surface and the outer surface.

* * * * *